(12) United States Patent
Raspallo

(10) Patent No.: US 6,874,504 B1
(45) Date of Patent: Apr. 5, 2005

(54) ENDOTRACHEAL TUBE

(76) Inventor: Louise D. Raspallo, 15 Louise F. Luther Dr., Cumberland, RI (US) 02864

( * ) Notice: Subject to any disclaimer, the term of this patent is extended or adjusted under 35 U.S.C. 154(b) by 0 days.

(21) Appl. No.: 10/375,019

(22) Filed: Feb. 28, 2003

(51) Int. Cl.$^7$ .............................................. A61M 16/00
(52) U.S. Cl. .............................. 128/207.14; 128/207.15
(58) Field of Search ....................... 128/200.26, 200.24, 128/207.14, 207.15, 207.16, 207.12, 207.18; 604/97.01–97.03, 98.02, 99.01–99.03, 915, 916, 96.01, 103.08, 103.06; 600/561

(56) References Cited

U.S. PATENT DOCUMENTS

| | | | |
|---|---|---|---|
| 3,363,629 A | | 1/1968 | Kuhn |
| 3,599,642 A | * | 8/1971 | Tindel ................... 128/207.14 |
| 3,964,488 A | | 6/1976 | Ring et al. |
| 4,622,965 A | * | 11/1986 | Teeple ................... 128/207.14 |
| 4,716,896 A | * | 1/1988 | Ackerman ............. 128/200.26 |
| 4,981,477 A | * | 1/1991 | Schon et al. ................ 604/264 |
| 5,033,466 A | * | 7/1991 | Weymuller, Jr. ....... 128/207.15 |
| 5,235,970 A | | 8/1993 | Augustine |
| 5,245,992 A | * | 9/1993 | Nye ....................... 128/200.26 |
| 5,333,608 A | * | 8/1994 | Cummins ............... 128/207.14 |
| 5,590,647 A | | 1/1997 | Nye |
| 5,819,733 A | | 10/1998 | Bertram |
| 6,321,749 B1 | | 11/2001 | Toti et al. |
| 6,705,320 B1 | * | 3/2004 | Anderson .............. 128/207.14 |

FOREIGN PATENT DOCUMENTS

DE        70351358        9/1970

* cited by examiner

Primary Examiner—Henry Bennett
Assistant Examiner—Teena Mitchell
(74) Attorney, Agent, or Firm—Fish & Richardson P.C.

(57) ABSTRACT

An endotracheal tube includes a proximal tube shaft and a distal tube shaft coupled to the proximal tube shaft. The proximal tube shape defines a proximal lumen and the distal tube shaft defines a distal lumen extending from the proximal lumen. The distal tube shaft includes two or more curved portions configured to be inserted into the trachea when the tube is inserted into a patient. The proximal tube shaft includes a substantially straight or a slightly curved portion. A method of intubating a patient includes advancing a tube having a distal portion with at least two curved portions into the trachea of the patient, and delivering gas through the tube to the patient's lungs.

31 Claims, 6 Drawing Sheets

ENDOTRACHEAL TUBE

TECHNICAL FIELD

This description relates to an endotracheal tube.

BACKGROUND

An endotracheal tube is used during surgery that requires respiratory assistance, typically for ventilation and/or the administration of inhalation anesthesia through a patient's opened vocal chords into the trachea. Additionally, an endotracheal tube can be used to assist ventilation of a patient experiencing a respiratory crisis. The endotracheal tube includes a connector that connects the endotracheal tube to a gas supply such that the gas flows from the supply through the tube to the lungs.

SUMMARY

In one general aspect, an endotracheal tube includes a proximal tube shaft and a distal tube shaft coupled to the proximal tube shaft. The proximal tube shaft defines a proximal lumen and the distal tube shaft defines a distal lumen extending from the proximal lumen. The distal tube shaft includes two or more curved portions that are configured to be inserted into the trachea when the tube is inserted into a patient.

Implementations may include one or more of the following features. For example, the proximal tube shaft includes a straight portion and an inlet at a proximal end of the shaft. The proximal lumen has a diameter sized to accommodate a stylet.

The proximal tube shaft is made from a material that is able to return to its original premolded shape following a flexure. The distal tube shaft is made from a material that is able to return to an original premolded shape following a flexure. Either or both of the tube shafts are formed of a material that conforms to the shape of a patient's trachea. The shafts are formed, for example, of a flexible thermoplastic material.

The distal tube shaft is coupled to the proximal tube shaft by molding, by welding, or by gluing. The distal tube shaft may be coupled to the proximal tube shaft by integrally molding the distal tube shaft and the proximal tube shaft during manufacturing.

The distal tube shaft includes an inflatable cuff. The inflatable cuff covers at least a portion of the two or more curved portions of the distal tube shaft. The proximal tube shaft includes at least one curved portion.

In another general aspect, an endotracheal tube includes a proximal tube shaft defining a proximal lumen that extends along a central axis, and a distal tube shaft coupled to the proximal tube shaft and defining a distal lumen that extends along a central axis. The distal central axis includes one or more inflection points. The portions of the distal tube shaft on either side of the one or more inflection points are configured to be inserted into a trachea of a patient when the tube is inserted into the patient.

In another general aspect, a medical device includes a tube having a distal portion having at least two curved portions. The distal portion is configured for placement into a trachea of a patient. Implementations may include the following features. For example, the tube includes a proximal portion with a straight portion. The tube has an outer diameter in the range of about 0.6 to 2 cm. The tube has an outer diameter sized to fit within the trachea. The tube defines a lumen for passage of a gas. The lumen has a diameter in the range of about 2.5 to 9 mm.

In another general aspect, a method of intubating a patient includes advancing a tube having a distal portion with at least two curved portions into the trachea of the patient, and delivering gas through the tube to the patient's lungs. The method may further include maneuvering the tube without the use of a stylet.

In another general aspect, a method for making an endotracheal tube includes providing a tube having a proximal portion defining a lumen and a distal portion defining a lumen extending from the proximal lumen, and forming the distal portion to include two or more curved portions. The method may further include forming the proximal portion with a straight portion and forming the distal portion to fit within a trachea of a patient when the tube is inserted into the patient. The method may also include forming an inflatable cuff over a portion of the two or more curved portions of the distal portion.

Aspects of the techniques and systems may include one or more of the following advantages. For example, the shape of the distal tube shaft, with the two or more curved portions, facilitates intubation of the patient's trachea by enhancing maneuverability within the laryngeal cavity during insertion. Furthermore, the shape of the distal tube shaft is contoured to track the shape of the trachea, thus limiting the risk of injury due to puncture of soft tissue surrounding the trachea. If a stylet is used, the operator inserts the stylet into the proximal tube shaft up to the distal tube shaft, but the operator need not insert the stylet within the distal tube shaft. Thus, the risk of injury is reduced because the tissue of the trachea is contacted by the relatively soft distal end of the tube rather than the end of a stylet, which can accidentally protrude from the tube if the stylet is positioned within the distal tube shaft.

Other features and advantages will be apparent from the description, the drawings, and the claims.

DESCRIPTION OF DRAWINGS

Like reference symbols in the various drawings indicate like elements.

DETAILED DESCRIPTION

Figure 1:
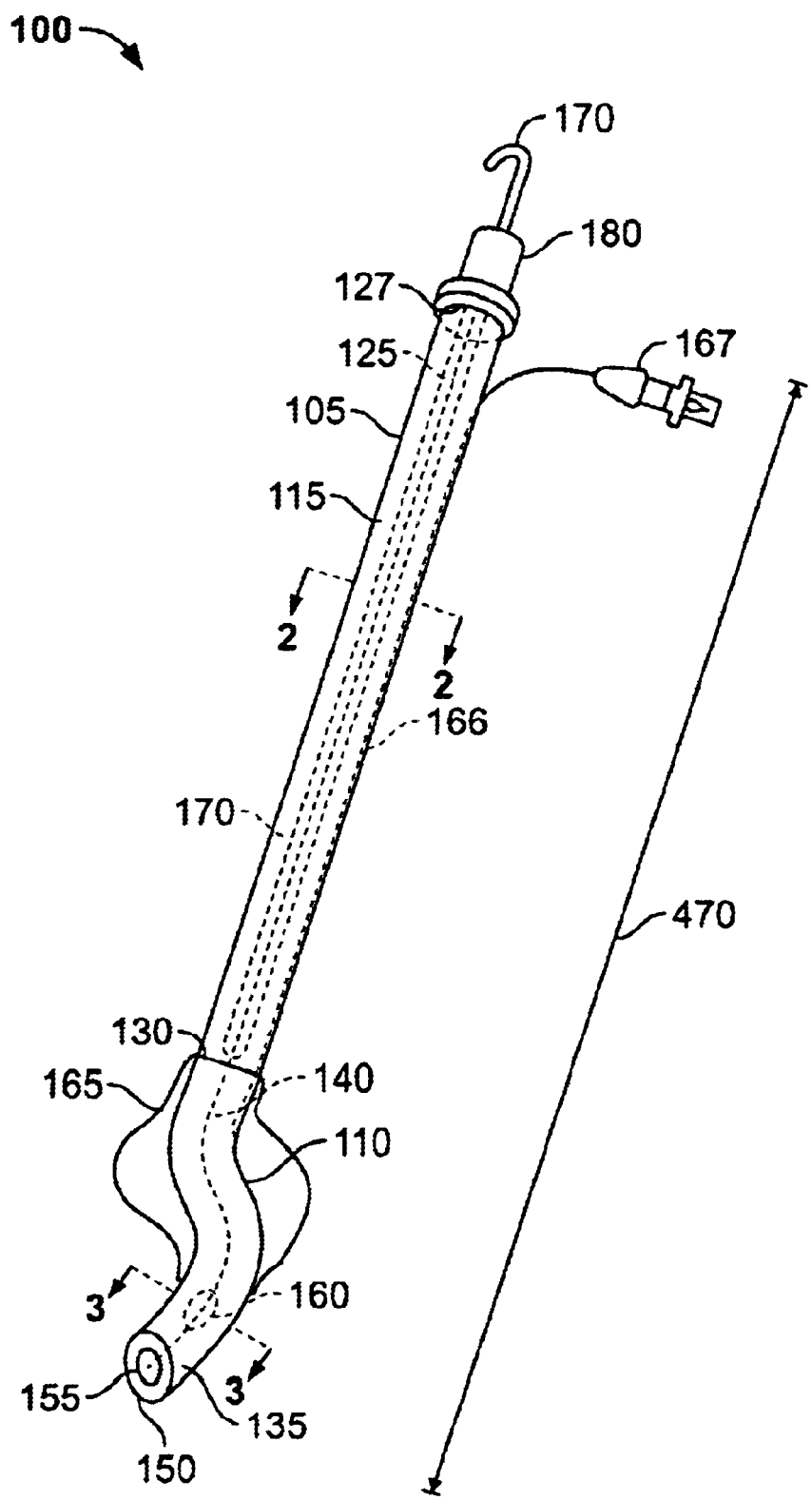
FIG. 1 shows an endotracheal tube according to the invention.
Figure 2:
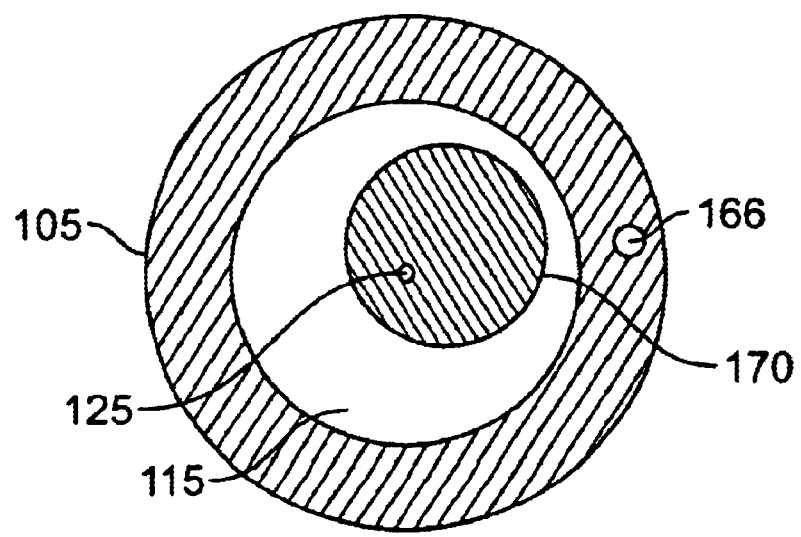
FIG. 2 shows a cross-sectional view of the endotracheal tube of FIG. 1 taken along section 2—2.
Figure 3:
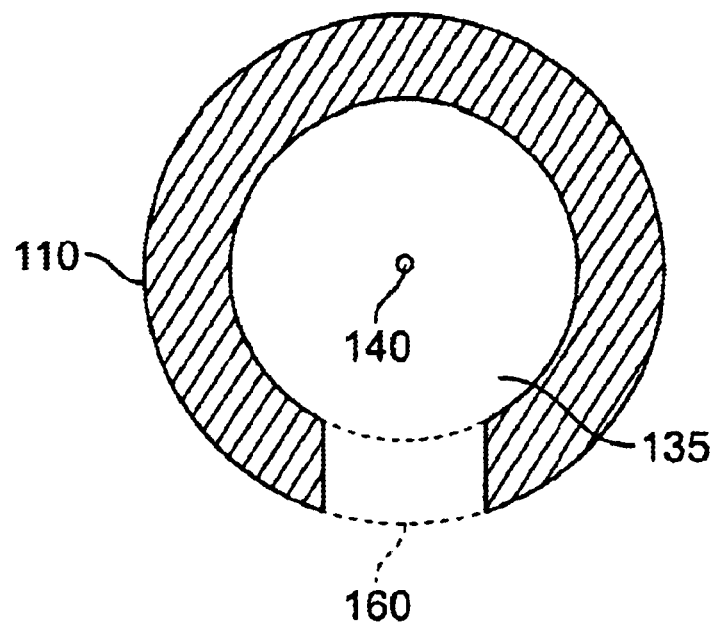
FIG. 3 shows a cross-sectional view of the endotracheal tube of FIG. 1 taken along section 3—3.

Referring to FIG. 1, an endotracheal tube 100 includes a proximal tube shaft 105, which is nearer the operator, and a distal tube shaft 110, which is inserted into the trachea of a patient. The distal tube shaft 110 connects with the proximal tube shaft 105 at an imaginary plane (depicted by line 130). The proximal tube shaft 105 has a central axis 125 (see also FIG. 2). The distal tube shaft 110 has a central axis 140 (see also FIG. 3). The two axes meet at the plane 130. The proximal tube shaft 105 is shaped with a substantially straight or a slightly curved portion, as described further below. The distal tube shaft 110 is shaped with a first curved portion that is concave in a first direction and a second curved portion that is concave in a second direction distinct from the first direction, as described further below. The shape of the distal tube shaft provides, in three dimensions, flexibility, movement and control of the distal region of the endotracheal tube. This provides for safe, efficient, and quick intubation, that is, insertion of the endotracheal tube (in particular, the distal region of the endotracheal tube) into the trachea.

The proximal tube shaft 105 defines a proximal lumen 115 and an inlet 127 for flow of gas into the proximal lumen 115. The distal tube shaft 110 defines a distal lumen 135 in fluid communication with the proximal lumen 115 for flow of gas from the proximal lumen 115 to the distal lumen 135. The distal tube shaft 110 terminates in a beveled end 150 having an outlet 155 for flow of gas out of the distal lumen 135. Additionally, the distal tube shaft 110 defines an opening 160 through the wall of the tube for flow of gas out of the distal lumen 135.

The endotracheal tube 100 typically includes an inflatable cuff 165 on the exterior of the distal tube shaft 110 near the plane 130. When inflated, the cuff 165 hugs the interior walls of the trachea to maintain the position of the endotracheal tube 100 within the trachea. The inflatable cuff 165 is inflated through a channel 166 that is separately formed within the proximal tube shaft 105 (see also FIG. 2). The channel 166 is connected to a checking device 167 for regulating the inflation pressure of the cuff 165. The endotracheal tube 100 also includes a connector 180 (for example, a Luer-locking connection) on the proximal tube shaft 105 that connects to a gas supply (not shown).

Figure 4:
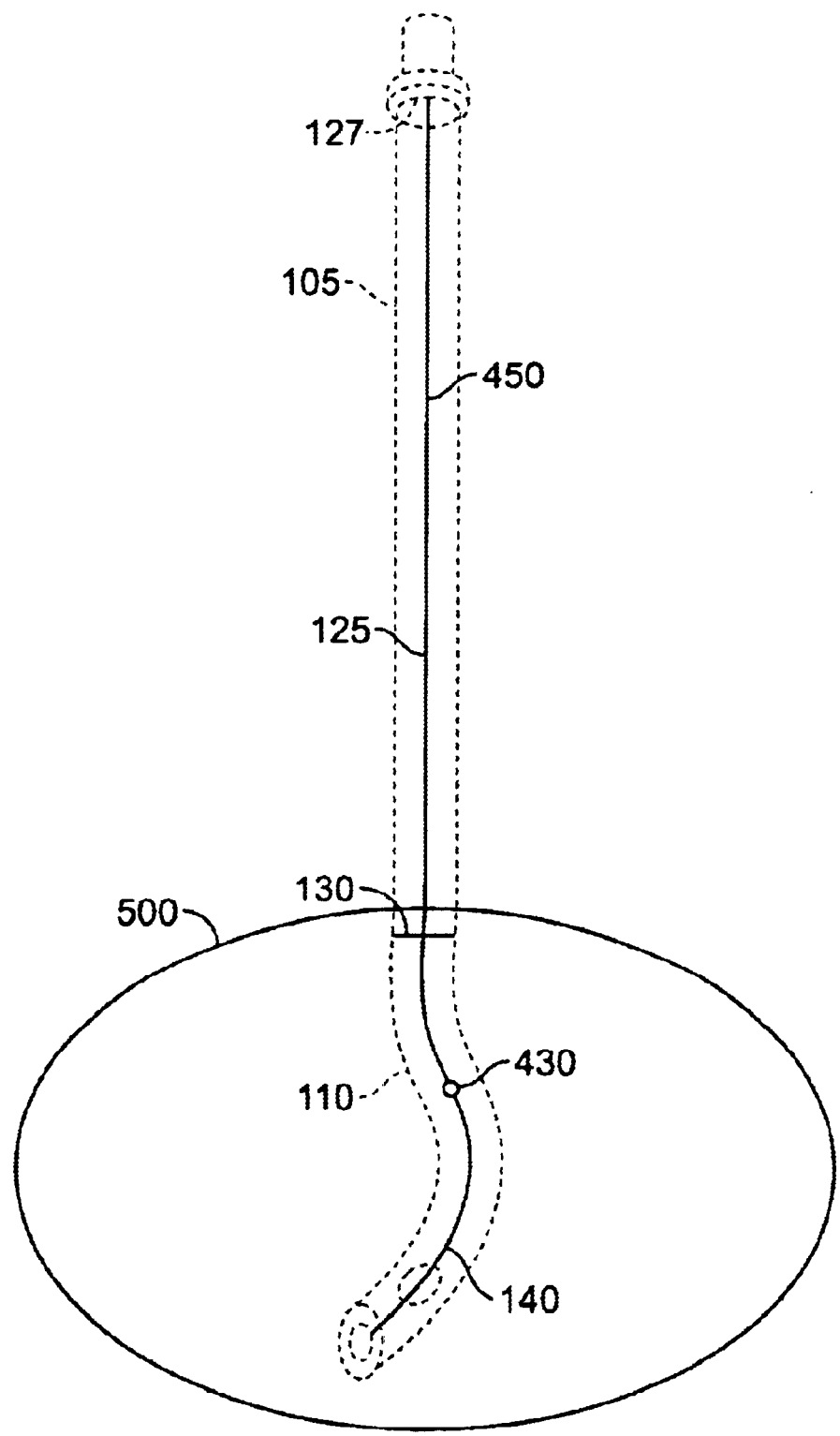
FIG. 4 shows the curvature of the endotracheal tube of FIG. 1.

Referring to FIG. 4, the proximal tube shaft 105 is shaped with a substantially straight or a slightly curved portion 450.

Figure 5:
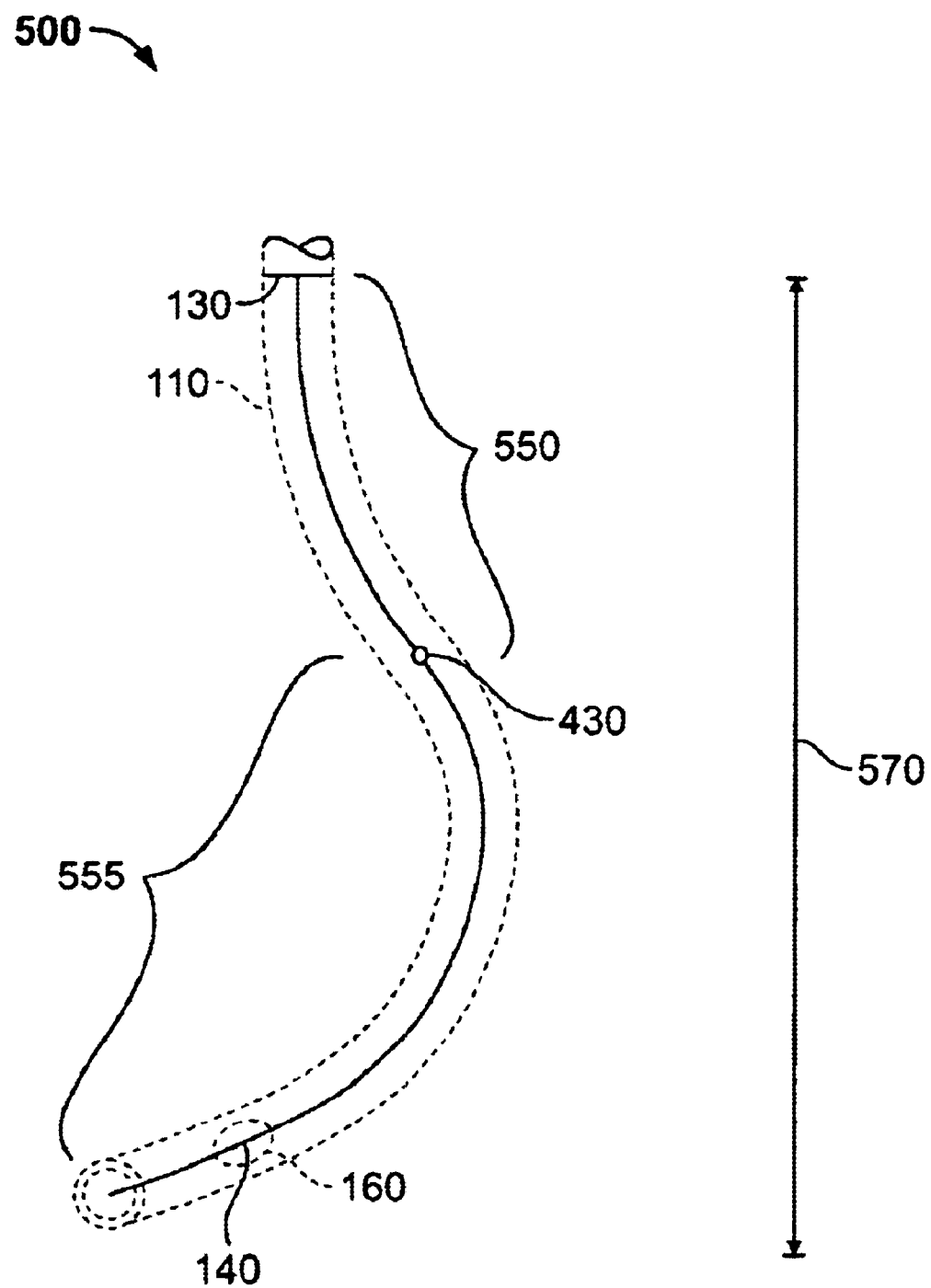
FIG. 5 shows the curvature of a distal portion of the endotracheal tube of FIG. 1.

Referring also to FIG. 5, the distal tube shaft 110 is shaped with two or more curved portions 550, 555 such that the distal axis 140 is concave in two or more distinct directions. For example, curved portion 550 is concave as viewed from the right in FIG. 5, and curved portion 555 is concave as viewed from the left in FIG. 5. Therefore, the distal axis 140 passes through at least one inflection point (such as point 430), which defines the plane at which the curved portion 550 meets the curved portion 555. Along the curved portion 550, the axis 140 follows a curve having a radius of curvature suitable with the size and shape of the trachea into which the distal tube shaft 110 is inserted. Along the curved portion 555, the axis 140 follows a curve having a radius of curvature suitable to the size and shape of the trachea into which the distal tube shaft 110 is inserted. The curved portion 550 is preferably oriented opposite to the curved portion 555, as shown in the figures. Thus, the amount of bend in the curved portions 550, 555 is limited by the size of the trachea. For simplicity, the axis 140 is shown to traverse a two-dimensional path; however, the axis 140 may traverse a three-dimensional path.

The tube shafts 105 and 110 are each made from materials having sufficient memory and resiliency to return to their respective premolded shapes following a flexure. Additionally, the tube shafts 105 and 110 are made from materials that enable the tube shafts 105 and 110 to conform to the shape of the patient's laryngeal cavity and trachea, rather than forcing the trachea to conform to the shapes of the tube shafts 105 and 110. The materials are selected such that the tube shafts 105 and 110 do not kink during use. The tube shafts 105 and 110 can be molded individually as separate pieces and then joined together using any suitable technique, such as, for example, a glue seal, a weld seal, a mold, or an interference fit. The joining technique can be selected depending on the materials selected for the tube shafts 105 and 110. Alternatively, tube shafts 105, 110 can be molded from a single tube.

Suitable materials for the tube shafts 105 and 110 include flexible thermoplastic materials such as, for example, polyvinylchloride, and polyethylene. Furthermore, the distal tube shaft 110 can be made from a material that is rigid enough to retain its shape upon entering the patient's trachea, soft enough to prevent injury to the patient's trachea and to prevent kinking of the shaft 110.

The distal tube shaft 110 is sized to fit within the trachea, which can vary in diameter from 0.5 to 2.5 cm. Accordingly, the outer diameter of the distal tube shaft 110 will be smaller than the smallest diameter of the trachea of the patient to be anesthetized. For example, the outer diameter of distal tube shaft 110 can range between approximately 0.6 to 2 cm. The distal tube shaft 110 has a length (labelled as 570 as shown in FIG. 5) and the tube 100 has a total length (labelled as 470 as shown in FIG. 1) to enable the operator to insert the entire distal tube shaft 110 into the trachea upon insertion of the tube 100 into the patient. In this way, at least a portion of each of the curved portions 550, 555 is covered by the inflatable cuff 165. For example, the size of the distal tube shaft 110 and the tube 100 are selected depending on the patient's age, sex, and/or size. In one implementation, the length 570 of the distal tube shaft 110 is about 5 cm and the total length 470 of the tube 100 is about 32 cm for use in an adult trachea. The total length 470 of the tube 100 is about 20 cm long for use in the trachea of a child. The lumens 115, 135 have a diameter, for example, of about 2.5 to 9 mm, for permitting an adequate supply of gas to flow to the patient's lungs, and for receiving a stylet, as described below.

Figure 6:
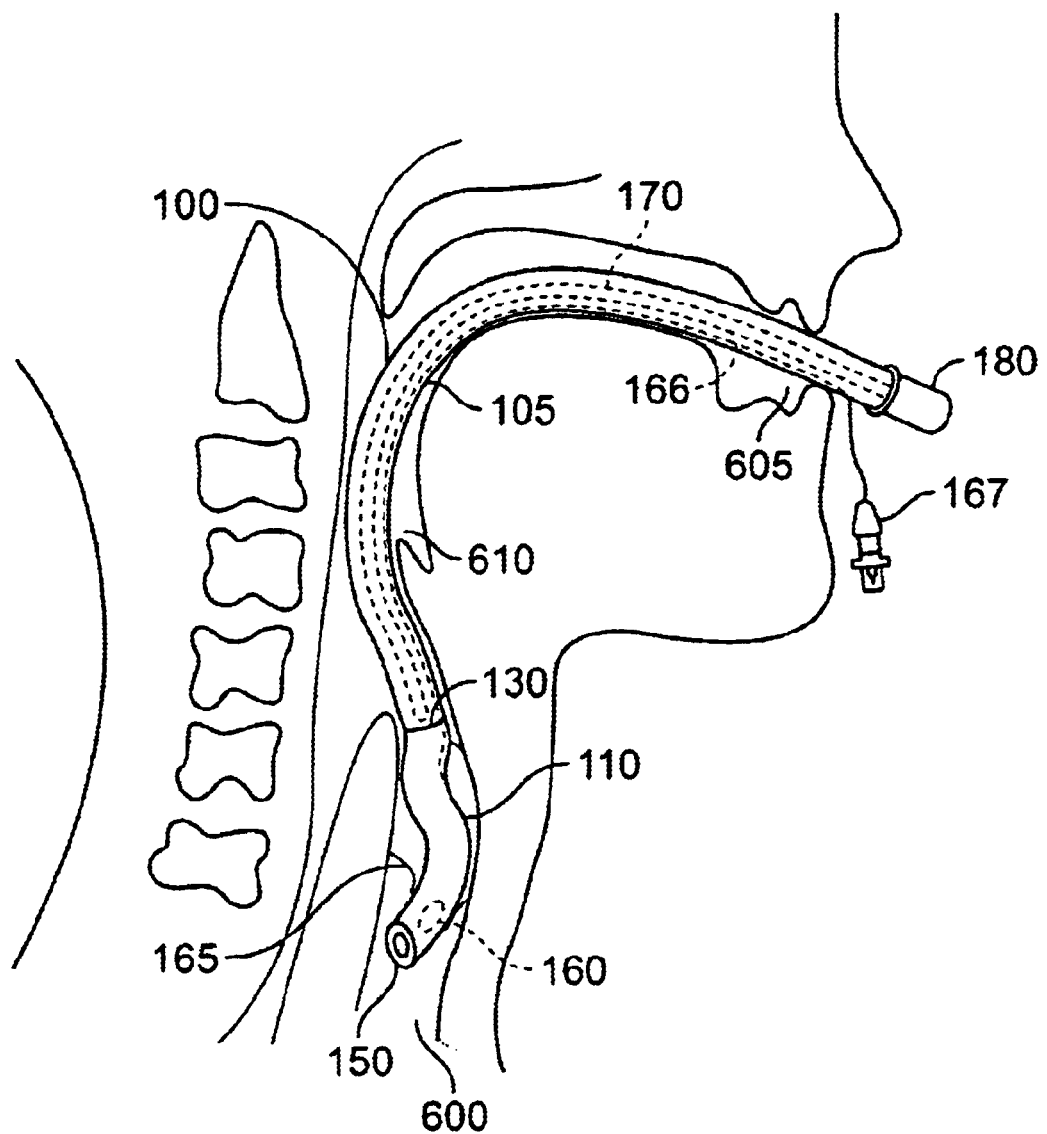
FIG. 6 shows the endotracheal tube of FIG. 1 inserted into a patient.

Referring to FIG. 6, in use, the operator inserts the beveled end 150 of the tube 100 into the mouth 605 of the patient and maneuvers the distal tube shaft 110 through the laryngeal cavity 610 and into the trachea 600. During insertion, the operator can use an optical device such as a light source or a telescope or a mechanical guide device to maneuver the distal tube shaft 110 through the laryngeal cavity 610 and into the trachea 600. The operator then attaches the anesthesia supply (not shown) to the connector 180 of the tube 100.

The operator inflates the cuff 165 after intubation or at any suitable time during intubation. In this way, the cuff 165 functions to hug the wall of the trachea and to protect the trachea and lungs against aspiration of foreign substances, such as foreign bodies, food, or digestive system contents. The operator then administers oxygen or inhalation anesthesia directly to the patient through the outlet 155 and the opening 160. The opening 160 serves to ventilate the inhalation anesthesia if the outlet 155 becomes clogged.

Referring again to FIG. 1, though not required, during a procedure a stylet 170 can be used in conjunction with the endotracheal tube 100. The stylet 170 is a semi-rigid wire, which maintains a preformed shape until bent into another shape. The stylet 170 is sized to be received within lumens 115, 135. The operator inserts the stylet 170 into the proximal lumen 115 of the proximal tube shaft 105 until the stylet 170 is at or near the plane 130. The operator can bend the stylet 170 into a desired shape after insertion into the endotracheal tube 100. The stylet 170 provides rigidity to the otherwise flexible endotracheal tube 100, thus facilitating insertion of the proximal tube shaft 105 into the laryngeal cavity 610 of the patient. The operator need not insert the stylet 170 into the distal tube shaft 110 because the shape of the distal tube shaft 110 facilitates its passage into the trachea 600. In this way, the risk of injury to soft tissue and vocal chords surrounding the trachea is reduced because the end of the stylet is prevented from reaching the end 150 of the insertion within the tube 100.

The operator uses the stylet 170 to guide the distal tube shaft 110 during insertion of the beveled end 150 into the mouth 605 of the patient and maneuvering of the distal tube shaft 110 through the laryngeal cavity 610 and into the trachea 600. The operator removes the stylet 170 from the endotracheal tube 100 when the tube 100 enters the vocal chords.

Figure 7:
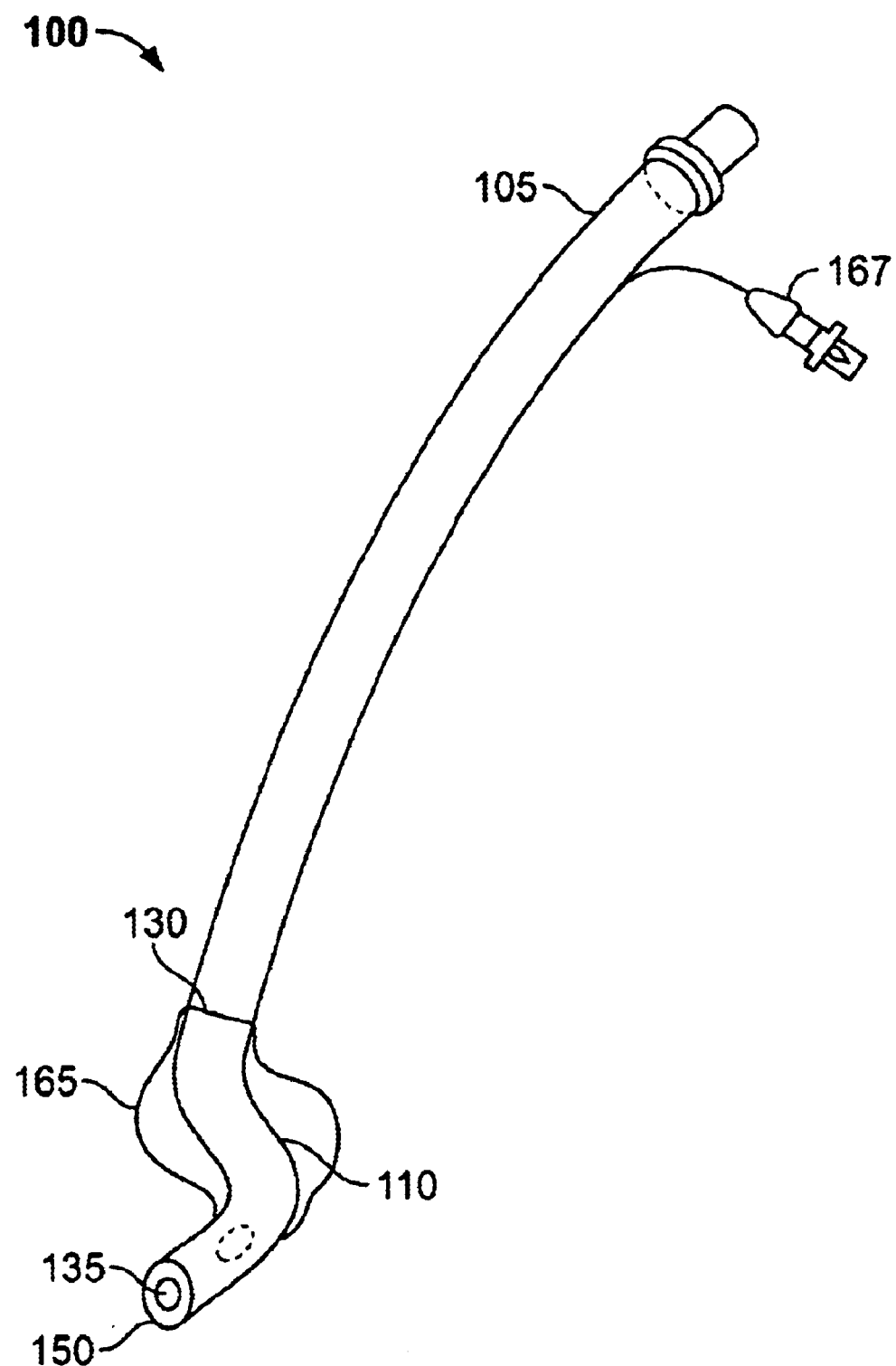
FIG. 7 shows an endotracheal tube according to the invention.

Other implementations are within the scope of the following claims. For example, the proximal tube shaft 105 may include one or more curved portions. For example, as shown in FIG. 7, the proximal tube shaft 105 has a curved portion that is concave in a single direction. The tube shafts 105 and 110 can be molded as a single piece.

What is claimed is:

1. An endotracheal tube comprising:
   a proximal tube shaft defining a proximal lumen;
   a distal tube shaft coupled to the proximal tube shaft and defining a distal lumen extending from the proximal lumen, the distal tube shaft including two or more curved portions having concavities with distinct directions, the curved portions being configured to be inserted into the trachea when the tube is inserted into a patient; and
   a device that covers at least a portion of the two or more curved portions of the distal tube shaft configured to maintain the position of the tube within the trachea.

2. The tube of claim 1 wherein the proximal tube shaft includes a straight portion.

3. The tube of claim 1 wherein the proximal tube shaft includes an inlet at a proximal end of the proximal tube shaft.

4. The tube of claim 1 wherein the proximal lumen has a cross-section sized to accommodate a stylet.

5. The tube of claim 1 wherein the proximal tube shaft is made from a material that is able to return to an original premolded shape following a flexure.

6. The tube of claim 1 wherein the distal tube shaft is made from a material that is able to return to its original premolded shape following a flexure.

7. The tube of claim 1 wherein the proximal tube shaft is formed of a material that conforms to the shape of a patient's trachea.

8. The tube of claim 1 wherein the distal tube shaft is formed of a material that conforms to the shape of a patient's trachea.

9. The tube of claim 1 wherein the proximal tube shaft is formed of a flexible thermoplastic material.

10. The tube of claim 1 wherein the distal tube shaft is formed of a flexible thermoplastic material.

11. The tube of claim 1 wherein the distal tube shaft is coupled to the proximal tube shaft by molding.

12. The tube of claim 1 wherein the distal tube shaft is coupled to the proximal tube shaft by welding.

13. The tube of claim 1 wherein the distal tube shaft is coupled to the proximal tube shaft by gluing.

14. The tube of claim 1 wherein the distal tube shaft and the proximal tube shaft are integrally molded as a single piece.

15. The tube of claim 1 wherein the distal tube shaft includes an inflatable cuff.

16. The tube of claim 1 wherein the proximal tube shaft includes at least one curved portion.

17. An endotracheal tube comprising:
    a proximal tube shaft defining a proximal lumen that extends along a central axis; and
    a distal tube shaft coupled to the proximal tube shaft and defining a distal lumen that extends along a central axis;
    wherein, the distal central axis includes one or more inflection points and portions of the distal tube shaft on either side of the one or more inflection points are configured to be insertedv into the trachea when the tube is inserted into a patient;
    wherein the distal tube shaft includes a device covering the at least one of the one or more inflection points configured to maintain the position of the tube within the trachea.

18. An endotracheal tube, comprising:
    a tube including a distal portion having at least two curved portions having concavities with distinct directions, the curved portions being configured for placement into a trachea of a patient; and
    a device covering at least a portion of the at least two curved portions of the distal portion configured to maintain the position of the curved portions within the trachea.

19. The medical device of claim 18 wherein the tube includes a proximal portion with a straight portion.

20. The medical device of claim 18 wherein the tube includes a proximal portion with at least one curve.

21. The medical device of claim 18 wherein the tube has an outer diameter sized to fit within the trachea.

22. The medical device of claim 18 wherein the tube has an outer diameter in the range of 0.6 to 2 cm.

23. The medical device of claim 18 wherein the tube defines a lumen for passage of a gas.

24. The medical device of claim 18 wherein the lumen has a diameter in the range of 2.5 to 9 mm.

25. A method for making an endotracheal tube, the method comprising:
    providing a tube having a proximal portion defining a lumen and a distal portion defining a lumen extending from the proximal lumen,
    forming the distal portion to include two or more curved portions having a concavities with distinct directions, the curved portions being configured for placement within a trachea of a patient, and
    forming a device over a portion of the two or more curved portions, the device configured to maintain the position of the tube within the trachea when the tube is placed within the trachea.

26. The method of claim 25 further comprising forming the proximal portion with a straight portion.

27. A method of intubating a patient, comprising:
    advancing an endotracheal tube having a distal portion with at least two curved portions having concavities with distinct directions into the trachea of the patient, and
    delivering gas through the tube to the patient's lungs.

28. The method of claim 27 wherein advancing includes maneuvering the tube without the use of a stylet.

29. The tube of claim 1 wherein the device is an inflatable cuff.

30. The tube of claim 17 wherein the device is an inflatable cuff.

31. The method of claim 25 wherein forming the device includes forming an inflatable cuff over the portion of the two or more curved portions.

* * * * *